(12) United States Patent
Parramon et al.

(10) Patent No.: US 9,446,250 B2
(45) Date of Patent: *Sep. 20, 2016

(54) IMPLANTABLE MEDICAL DEVICE WITH MULTI-FUNCTION SINGLE COIL

(71) Applicant: Boston Scientific Neuromodulation Corporation, Valencia, CA (US)

(72) Inventors: Jordi Parramon, Valencia, CA (US); Matthew I. Haller, Valley Village, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/880,011

(22) Filed: Oct. 9, 2015

(65) Prior Publication Data

US 2016/0030755 A1   Feb. 4, 2016

Related U.S. Application Data

(60) Continuation of application No. 14/327,065, filed on Jul. 9, 2014, now Pat. No. 9,155,898, which is a continuation of application No. 13/420,830, filed on Mar. 15, 2012, now Pat. No. 8,781,596, which is a continuation of application No. 12/623,758, filed on Nov. 23, 2009, now Pat. No. 8,155,752, which is a continuation-in-part of application No. 12/099,474, filed on Apr. 8, 2008, now Pat. No. 7,904,171, which is a division of application No. 11/047,052, filed on Jan. 31, 2005, now Pat. No. 7,379,775, which is a continuation of application No. 10/679,621, filed on Oct. 6, 2003, now Pat. No. 6,856,838, which is a continuation of application No. 09/799,467, filed on Mar. 5, 2001, now Pat. No. 6,631,296.

(60) Provisional application No. 60/189,992, filed on Mar. 17, 2000.

(51) Int. Cl.
*A61N 1/00* (2006.01)
*A61N 1/372* (2006.01)
*A61N 1/378* (2006.01)

(52) U.S. Cl.
CPC .......... *A61N 1/37223* (2013.01); *A61N 1/378* (2013.01); *A61N 1/3787* (2013.01); *A61N 1/37229* (2013.01); *A61N 1/3727* (2013.01); *A61N 1/37205* (2013.01)

(58) Field of Classification Search
CPC ..................... A61N 1/37205; A61N 1/37223; A61N 1/37229; A61N 1/3727; A61N 1/378; A61N 1/3787
See application file for complete search history.

(56) References Cited

U.S. PATENT DOCUMENTS

| | | | |
|---|---|---|---|
| 3,229,684 A | 1/1966 | Nagumo et al. | |
| 3,758,865 A | 9/1973 | McKibben | |
| 3,796,221 A | 3/1974 | Hagfors | |
| 4,082,097 A * | 4/1978 | Mann ................... | A61N 1/3787 320/108 |

(Continued)

*Primary Examiner* — George Manuel
(74) *Attorney, Agent, or Firm* — Lewis, Reese & Nesmith, PLLC

(57) ABSTRACT

A combination charging and telemetry circuit for use within an implantable device, such as a microstimulator, uses a single coil for both charging and telemetry. In accordance with one aspect of the invention, one or more capacitors are used to tune the single coil to different frequencies, wherein the coil is used for multiple purposes, e.g., for receiving power from an external source and also for the telemetry of information to and from an external source.

20 Claims, 9 Drawing Sheets

(56) References Cited

U.S. PATENT DOCUMENTS

| | | |
|---|---|---|
| 4,197,850 A | 4/1980 | Schulman et al. |
| 4,345,604 A | 8/1982 | Renirie |
| 4,453,162 A | 6/1984 | Money et al. |
| 4,679,560 A | 7/1987 | Galbraith |
| 5,324,315 A | 6/1994 | Grevious |
| 5,324,316 A | 6/1994 | Schulman et al. |
| 5,405,367 A | 4/1995 | Schulman et al. |
| 5,480,415 A | 1/1996 | Cox et al. |
| 5,522,865 A | 6/1996 | Schulman et al. |
| 5,630,836 A | 5/1997 | Prem et al. |
| 5,658,319 A | 8/1997 | Kroll |
| 5,674,264 A | 10/1997 | Carter et al. |
| 5,713,939 A | 2/1998 | Nedungadi et al. |
| 5,733,313 A | 3/1998 | Barreras, Sr. et al. |
| 5,741,316 A | 4/1998 | Chen et al. |
| 5,769,877 A | 6/1998 | Barreras, Sr. |
| 5,807,397 A | 9/1998 | Barreras |
| 5,814,089 A | 9/1998 | Stokes et al. |
| 5,991,664 A | 11/1999 | Seligman |
| 6,051,017 A | 4/2000 | Loeb et al. |
| 6,185,452 B1 | 2/2001 | Schulman et al. |
| 6,185,460 B1 | 2/2001 | Thompson |
| 6,516,227 B1 | 2/2003 | Meadows et al. |
| 6,549,807 B1 | 4/2003 | Kroll |
| 6,631,296 B1 | 10/2003 | Parramon et al. |
| 6,856,838 B2 | 2/2005 | Parramon et al. |
| 7,177,698 B2 | 2/2007 | Klosterman et al. |
| 7,379,775 B2 | 5/2008 | Parramon et al. |
| 7,428,438 B2 | 9/2008 | Parramon et al. |
| 8,010,205 B2 | 8/2011 | Rahman et al. |
| 8,081,925 B2 | 12/2011 | Parramon et al. |
| 8,335,569 B2 | 12/2012 | Aghassian |
| 8,498,716 B2 | 7/2013 | Chen et al. |
| 8,577,474 B2 | 11/2013 | Rahman et al. |
| 2011/0112611 A1 | 5/2011 | Aghassian |

* cited by examiner

T2/T1 = DUTY CYCLE

| MODE | M1' | M2 | M3 | M4 | M5 |
|---|---|---|---|---|---|
| STEP UP | ON | OFF | PWM ON | OFF | OFF |
| STEP DOWN | OFF | PWM ON | OFF | OFF | OFF |
| ENERGY RECEIVE | OFF | OFF | OFF | ON | ON |
| DATA RECEIVE | OFF | OFF | OFF | ON | ON |
| DATA XMIT | ON | OFF | MODULATION ON | ON | ON |

FIG. 8

| MODE | M6 | M7 | M8 | M9 |
|---|---|---|---|---|
| ENERGY RECEIVE | OFF | OFF | ON | OFF OR MODULATED (LSK) |
| DATA RECEIVE | OFF | ON | OFF | OFF |
| DATA XMIT | ON | MODULATED | OFF | OFF |

*Figure 10*

IMPLANTABLE MEDICAL DEVICE WITH MULTI-FUNCTION SINGLE COIL

CROSS-REFERENCE TO RELATED APPLICATIONS

The present application is a continuation of U.S. application Ser. No. 14/327,065, filed Jul. 9, 2014 (now U.S. Pat. No. 9,155,898), which is a continuation of U.S. application Ser. No. 13/420,830, filed Mar. 15, 2012 (now U.S. Pat. No. 8,781,596), which is a continuation of U.S. application Ser. No. 12/623,758, filed Nov. 23, 2009 (now U.S. Pat. No. 8,155,752), which was a continuation-in-part of U.S. application Ser. No. 12/099,474, filed Apr. 8, 2008 (now U.S. Pat. No. 7,904,171), which was a divisional of U.S. application Ser. No. 11/047,052, filed Jan. 31, 2005 (now U.S. Pat. No. 7,379,775), which was a continuation of U.S. patent application Ser. No. 10/679,621, filed Oct. 6, 2003 (now U.S. Pat. No. 6,856,838), which was a continuation of U.S. application Ser. No. 09/799,467, filed Mar. 5, 2001 (now U.S. Pat. No. 6,631,296), which claims the benefit of U.S. Provisional Application Ser. No. 60/189,992, filed Mar. 17, 2000. Priority is claimed to each of these applications, and each is incorporated by reference in their entireties.

BACKGROUND OF THE INVENTION

The present invention relates to implantable medical devices, and more particularly to a voltage converter for use within an implantable microstimulator, or similar implantable device, that uses an RF-powering coil instead of capacitors to provide a voltage step-up and step-down function. The present invention also relates to an implantable medical device with a single coil that can be used for both charging and the telemetry of information, potentially at two distinct frequencies.

Many implantable medical devices, such as neural stimulators, sensors, and the like, utilize a battery as a primary source of operating power. Other types of implantable devices, such as cochlear stimulators, rely on the presence of an alternating magnetic field to induce an ac voltage into the implantable device, where the induced voltage is thereafter rectified and filtered in order to provide the primary operating power for the device. In both types of devices—a battery-powered device or an RF-powered device—there is a frequent need to derive other operating voltages within the device from the primary power source. That is, there is a frequent need to step up the voltage of the primary power source to a higher voltage in order to, e.g., generate a high stimulation current or for some other purpose. Similarly, in some devices, there is also a frequent need to step down the voltage of the primary power source to a lower voltage for use in certain types of circuits in order to, e.g., conserve power.

In order to perform the voltage step-up or step-down function, it is known in the art to use a charge-pump voltage converter circuit. Charge pump circuits typically rely on a network of capacitors and switches in order to step up and step down a primary voltage source. For example, in order to step up a primary voltage source, a network of, e.g., four capacitors, may be connected in parallel through a switching network and maintained in the parallel connection configuration until each capacitor charges to the voltage of the primary power source. The voltage of the primary power source is, e.g., the battery voltage (where a battery is used as the primary power source). Once thus charged, the capacitors are switched so that they are connected in series, thereby effectively creating a voltage across the series connection that is four times the voltage of the primary voltage source. The charge associated with this higher voltage may then be transferred to another capacitor, e.g., a holding capacitor, and this process (or charging parallel-connected capacitors, switching them in series, and then transferring the charge from the series connection to a holding capacitor) is repeated as many times as is necessary in order to pump up the charge on the holding capacitor to a voltage that is four times as great as the voltage of the primary power source.

While charge-pump circuits have proven effective for performing step up and step down functions, such circuits require a large number of capacitors, which capacitors may be quite large and bulky. Charge pump circuits that use large numbers of bulky capacitors are not well suited for implantable medical devices that must remain very small. Moreover, charge pump circuits tend to be relatively slow and inefficient in operation. What is needed, therefore, is a voltage converter circuit that is able to perform the step up or step down function, efficiently, quickly, and without having to rely on the use of a large number of bulky capacitor/s.

SUMMARY OF THE INVENTION

The present invention addresses the above and other needs by providing a voltage converter for use within small implantable electrical devices, such as a microstimulator, that uses a coil, instead of capacitors, to provide the voltage step up and step down function. The output voltage of such converter is controlled, or adjusted, through duty-cycle and/or ON/OFF modulation. Hence, good efficiencies are achieved for virtually any voltage within the compliance range of the converter.

In accordance with one aspect of the invention, applicable to implantable devices having an existing RF coil through which primary or charging power is provided, the existing RF coil is used in a time-multiplexing scheme to provide both the receipt of the RF signal and the voltage conversion function. This minimizes the number of components needed within the device, and thus allows the device to be packaged in a smaller housing, or frees up additional space within an existing housing for other circuit components. The result is an implantable device having a voltage converter that may be much smaller and/or more densely packed than prior implantable devices.

In accordance with another aspect of the invention, the voltage up/down converter circuit is controlled by a pulse width modulation (PWM) and/or ON/OFF modulation (OOM) low power control circuit. Such operation advantageously allows high efficiencies over a wide range of output voltages and current loads.

According to another aspect of the invention, an implantable device containing a coil is provided, wherein the coil is used for multiple purposes, e.g., for receiving power from an external source and also as part of a voltage conversion circuit. Alternatively, or conjunctively, the coil may be used for receiving command information from an external source and also as part of a voltage conversion circuit.

It is thus a feature of the present invention to provide a voltage converter circuit for use within an implantable device, e.g., such as an implantable microstimulator or similar type of neural stimulator, that is compact, efficient, and provides a wide range of output voltages and currents.

It is a further feature of the invention to provide a voltage converter circuit that avoids the use of a network of capacitors switched between parallel and series, or other, configurations in order to provide the step up and step down voltage conversion function.

According to another aspect of the invention, an implantable device containing a single coil as well as one or more capacitors that are used to tune the coil to different frequencies is provided, wherein the different frequencies can be used to receiving power from an external source and for the telemetry of information to and from an external source.

BRIEF DESCRIPTION OF THE DRAWINGS

The above and other aspects, features and advantages of the present invention will be more apparent from the following more particular description thereof, presented in conjunction with the following drawings wherein:

FIG. 8 is a table that defines the operating state of the various switches M1', M2, M3, M4 and M5 utilized in the circuit of FIG. 7 in order to select a desired operating mode for the circuit shown in FIG. 7.

FIG. 10 is a table that defines the operating state of the various switches M6, M7, M8 and M9 utilized in the circuit of FIG. 9 in order to select a desired operating mode for the circuit shown in FIG. 9.

Corresponding reference characters indicate corresponding components throughout the several views of the drawings.

DETAILED DESCRIPTION OF THE INVENTION

Figure 1:
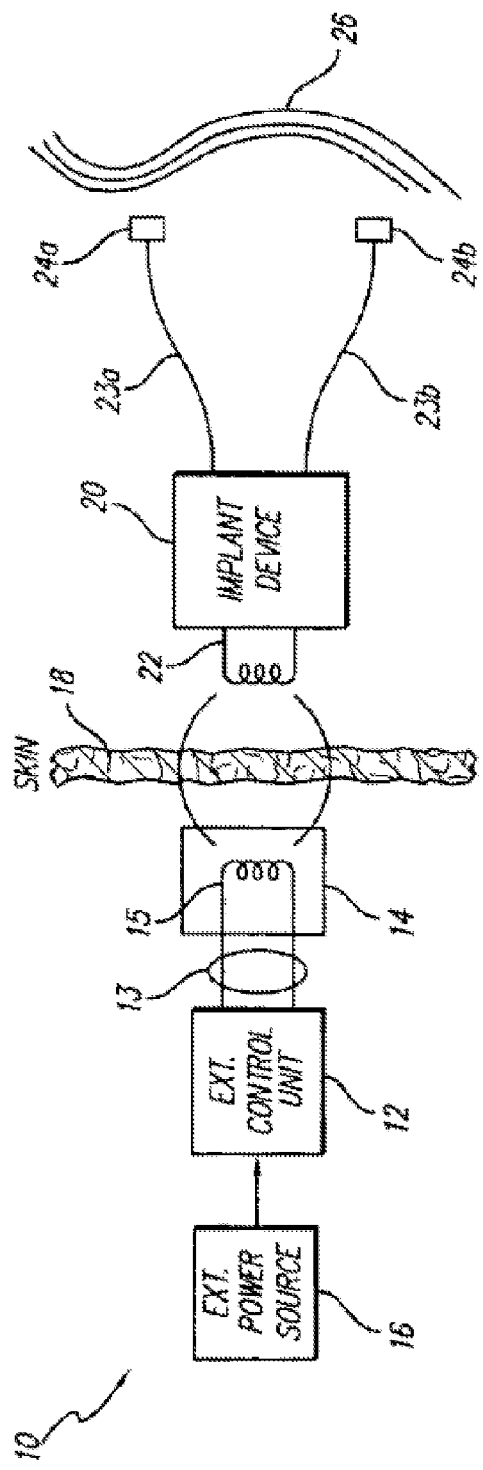
FIG. 1 is a block diagram of an implantable stimulator system.

The following description is of the best mode presently contemplated for carrying out the invention. This description is not to be taken in a limiting sense, but is made merely for the purpose of describing the general principles of the invention. The scope of the invention should be determined with reference to the claims.

The present invention relates to a particular type of voltage converter that may be used within an implantable medical device, such as an implantable stimulator, sensor, pump or other type of medical device providing a desired medical function. The invention will be described below in terms of an implantable stimulator, but it is to be understood that the invention may be used within many different types of implantable devices.

To better understand the environment in which the invention is intended to be used, it will first be helpful to review a typical implantable stimulation system. Hence, with reference to FIG. 1, a block diagram of a representative implantable stimulator system 10 is illustrated. The system 10 includes an implant device 20, implanted under the skin 18, coupled to an external control unit 12 through implanted coil 22 and external coil 15. The external coil 15 is typically carried in a housing 14 connected to the external control unit 12 via flexible cable 13. An external power source 16, which may be, e.g., a rechargeable or replaceable battery, provides operating power for the external control unit. The external power source 16 may also provide operating power for the implant device 20 through the link provided through the coils 15 and 22, either continuously or on an intermittent basis. Intermittent power is provided, e.g., such as when the implant device includes a replenishable power source, such as a rechargeable battery, and the battery is intermittently recharged.

The implant device 20, when functioning as a stimulator, includes a plurality of electrodes 24a and 24b connected to the implant device 20 via conductive leads or wires 23a and 23b, respectively. The electrodes 24a and 24b are typically implanted near body tissue or nerves 26 that are to be stimulated.

In operation, the system 10 functions as follows: The implant device 20 and electrodes 24a and 24b are implanted in the desired location under the patient's skin 18. It should be noted that while the implant coil 22 is shown separate from the implant device 20 in FIG. 1, the coil 22 is typically mounted to or housed within the same hermetically-sealed case used to house the electronic circuitry associated with the implant device 20. Once implanted, power and/or control data, e.g., programming data, is transferred to the implant device from the external control unit 12 via electromagnetic coupling between the implant coil 22 and the external coil 15. Once thus controlled or programmed, the implant device 20 operates as directed by the control signals received, or as steered by the program data stored therein, to generate electrical stimulation pulses for delivery to the tissue 26 via the electrodes 24a and 24b.

Some implant devices 20 do not contain an implanted power source, and such devices must thus receive their operating power continuously from the external control unit. Other implant devices 20 do contain an implanted power source, e.g., a rechargeable battery, and such devices thus receive their operating power from the implanted power source. However, on a regular or periodic basis, such devices must have the implanted power source replenished, e.g., have the battery recharged. Such recharging occurs via a link with the external control unit 12, or equivalent device, through the coils 22 and 15.

Figure 2:
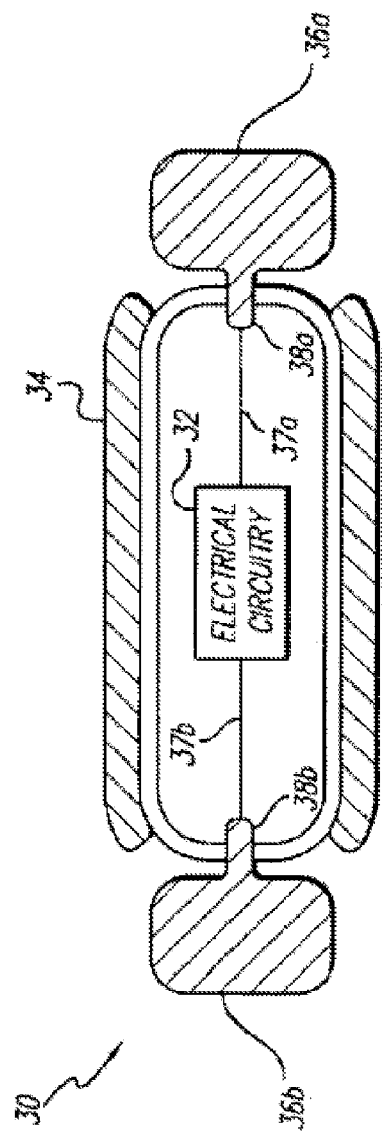
FIG. 2 is a sectional schematic diagram that illustrates one type of implantable microstimulator within which the present invention may be used.

FIG. 2 shows a sectional schematic diagram of one type of implantable microstimulator 30 within which the present invention may be used. The microstimulator device 30 includes electrical circuitry 32 housed within a hermetically-sealed case 34. At each end of the case 34 are electrodes 36a and 36b. These electrodes 36a and 36b are electrically connected to the electrical circuitry 32 via conductors, e.g., wires, 37a and 37b, respectively, and appropriate feed-through conductors 38a and 38b that pass through the wall of the hermetically-sealed case 34.

The advantage of the microstimulator device 30 is that it is very small, and can typically be easily implanted at the desired implant location through the lumen of a hypodermic needle, or other cannula. One embodiment of a microstimulator is disclosed, e.g., in U.S. Pat. No. 5,324,316, incorporated herein by reference. One method of making such a microstimulator is disclosed, e.g., in U.S. Pat. No. 5,405,367, also incorporated herein by reference.

Figure 3:
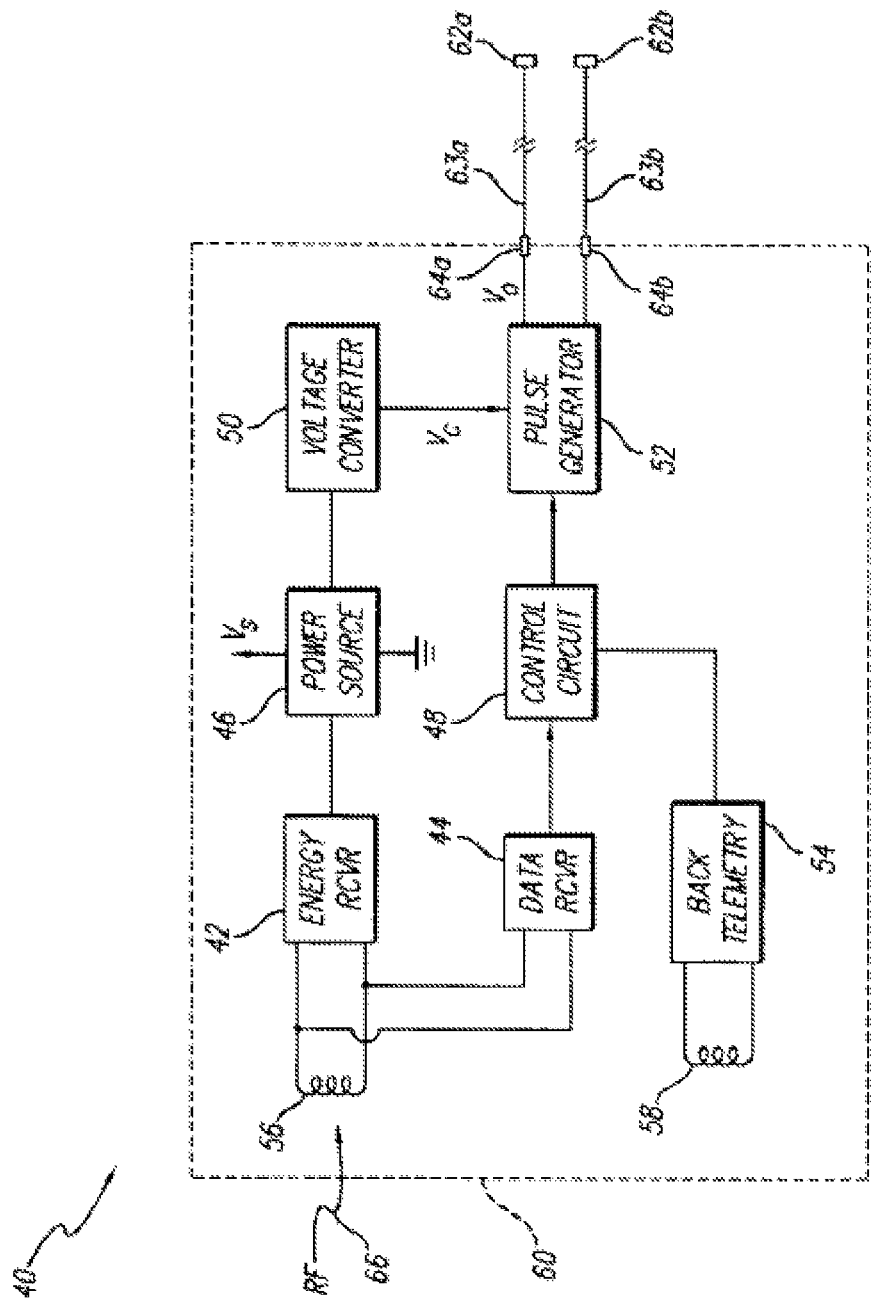
FIG. 3 is a functional block diagram of a typical implantable stimulator.

To better appreciate the advantages offered by the present invention, reference is next made to FIG. 3 where there is shown a functional block diagram of a typical implantable stimulator 40. As seen in FIG. 3, the stimulator 40 includes electronic circuitry that performs the following functions: an energy receiver 42, a data receiver 44, a power source 46, a control circuit 48, a voltage converter 50, a pulse generator 52, and a back telemetry circuit 54. An implanted coil 56 is connected to both the energy receiver 42 and the data receiver 44 and provides a means through which power and data signals may be received by the stimulator 40. Another coil 58, which in some embodiments may comprise the same, or a portion of, the coil 56, is connected to the back telemetry circuit 54, and provides a means through which back telemetry data may be sent to an external receiver. Such an external receiver may be included, for example, within the external control unit 12 (FIG. 1). All of the above-described elements of the stimulator 40 are housed within an hermetically-sealed housing or case 60, thereby allowing the stimulator 40 to be implanted within body tissue.

External to the housing 60, but still adapted to be implanted within body tissue, is a plurality of electrodes 62a, 62b. Electrical connection with the plurality of electrodes 62a, 62b is established through a plurality of wire conductors 63a, 63b (which may be included within a single implantable lead body, as is known in the art) which are respectively connected to a plurality of feed-through connectors 64a, 64b that pass through the hermetically-sealed wall of the case 60. The pulse generator 52 is electrically coupled to the plurality of feed-through connectors 64a, 64b on the inside of the case 60.

In operation, an RF signal (represented in FIG. 3 by the wavy arrow 66) is received through coil 56. Typically, the RF signal comprises a modulated carrier signal. The carrier signal is rectified in the energy receiver 42 and provides charging power for the power source 46. The carrier signal is demodulated in the data receiver 44 and the data thus recovered provides control and/or programming data to the control circuit 48. The control circuit 48, typically a microprocessor, includes memory circuitry (not shown) wherein programming and/or control data may be stored. Based on this programming and/or control data, the control circuit 48 drives the pulse generator circuit 52 so that it generates and delivers electrical stimulation pulses to the patient through selected groupings of the plurality of electrodes 62a, 62b.

In the process of generating the electrical stimulation pulses, which typically vary in amplitude as a function of the control and/or programming data, and in order to conserve power, it is necessary to provide a high level supply voltage to the pulse generator circuit 52. For example, if the impedance between electrodes 62a and 62b is 1000 ohms, and if a stimulation current pulse having a magnitude of 10 ma is desired, a voltage of 10 volts must be present at the electrodes 62a and 62b (Ohms law: voltage=current×impedance). This means that an output voltage VO of at least 10 volts must be present at the output of the pulse generator circuit 52. In turn, this means that a supply voltage VC, provided to the pulse generator circuit by the voltage converter 50, must be greater than 10 volts, e.g., 12 volts or more due to losses within the pulse generation circuit. Hence, the voltage converter circuit 50 is typically used in a stimulator 40 to step up the power source voltage VS, e.g., the battery voltage, to a level suitable for use by the pulse generator circuit 52. The power source voltage VS is typically a low value, e.g., 2 or 3 volts. Hence, in a typical stimulator device 40, such as the one shown in FIG. 3, the voltage converter circuit 50 is needed to boost, or step up, the source voltage VS from its relatively low value to a higher level VC as needed by the pulse generator circuit 52. Unfortunately, in order to provide such a step-up function, bulky and numerous circuit components, such as the capacitors used in a switched capacitor network, and/or transformers, must be employed.

The difference between the supply voltage VC and the output voltage VO may be referred to as the compliance voltage. In an ideal pulse generator circuit 52, the compliance voltage is kept as low as possible because the power dissipated in the pulse generator circuit (which is generally considered as wasted or lost power because it does not represent power delivered to the tissue) is proportional to the square of the compliance voltage. In practice, the compliance voltage cannot always be minimized because the current delivered through the electrodes 62a and 62b to the body tissue varies over a wide range; and hence the compliance voltage must also vary over a wide range.

In some implantable stimulators 40, in order to conserve the amount of power dissipated by the stimulator, the voltage converter circuit 50 is used to adjust the supply voltage VC, typically to provide a small number of discrete levels of supply voltage, as a function of the current to be delivered in the stimulation pulse. For example, a typical voltage converter circuit 50 may provide one of four different supply voltages VC to the pulse generator circuit 52, e.g., a VC of 2.5, 5.0, 7.5 or 10 volts, as a function of the programmed amplitude of the stimulation pulse that is to be delivered to the tissue. An implantable stimulator having such a feature is described, e.g., in U.S. Pat. No. 5,522,865, incorporated herein by reference.

It is thus seen that the voltage converter circuit 50 performs a very important function within the implantable stimulator 40. Unfortunately, however, the voltage converter circuit 50 represents additional circuitry that requires bulky circuit components, which takes up needed and valuable space within the case 60, and much of which also consumes additional power. Further, most voltage converter circuits 50 tend to be very inefficient. That is, a capacitor charge pump circuit, for example, typically may operate at efficiencies that may be less than 50%. Thus, for most stimulators, e.g., of the type shown in FIG. 2, space and power considerations are paramount to the design of the stimulator.

The present invention advantageously provides circuitry for use within an implantable stimulator device that performs the voltage conversion function using fewer and less bulky components. This frees up valuable space within the case of the stimulator that may be used for other functions (or allows the case to be smaller), and consumes less power than has heretofore been achievable. Additionally, the present invention provides a circuit that performs multiple functions, thus allowing fewer circuit components to be used within the stimulator design, thereby permitting the overall stimulator design to be smaller or more compact.

Figure 4:
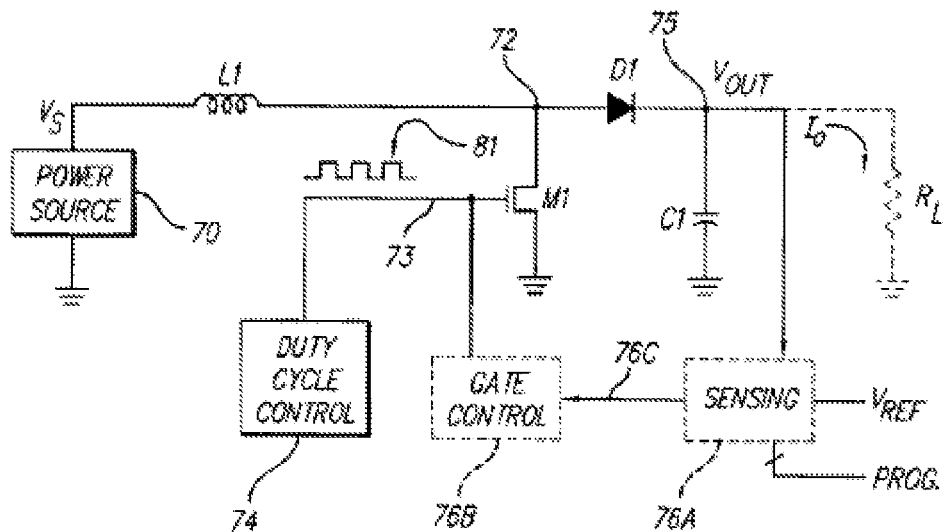
FIG. 4 illustrates a type of fly back converter circuit that may be used to step up the voltage of a power source without the use of a switched capacitor network.

Turning next to FIG. 4, a type of fly back converter circuit is illustrated that may be used to step up the voltage of a power source without the need for a switched capacitor network. The fly back circuit shown in FIG. 4 includes an inductor or coil L1 having one end connected to a power source 70. The other end of the coil L1 is connected to a first circuit node 72. A switching transistor M1 is connected between the first node 72 and ground. The transistor M1 has a gate terminal 73 connected to a duty cycle control circuit 74. When the transistor M1 is turned ON, through application of a signal to its gate terminal 73, node 72 is effectively switched to ground potential through a very low impedance path. When transistor M1 is turned OFF, through absence of a signal applied to its gate terminal 73, it represents a very high impedance path, and thus effectively maintains node 72 disconnected from ground.

Also connected to node 72 of the fly back circuit shown in FIG. 4 is the cathode side of diode D1. The anode side of diode D1 is connected to an output node 75. An output capacitor C1 is connected between the output node 75 and ground. A load, represented in FIG. 4 by phantom resistor RL, is also connected between the output node 75 and ground.

Still with reference to FIG. 4, the duty cycle control circuit 74 applies a pulsed signal to the gate of transistor M1, thereby effectively turning transistor M1 ON and OFF as controlled by the pulsed signal. For example, a high voltage applied to the gate of M1 may turn M1 ON (provide a low impedance path between node 72 and ground), and a low voltage applied to the gate of M1 may turn M1 OFF (provide a high impedance path between node 72 and ground). A sequence of high and low voltages may be applied to the gate 73 of transistor M1 through application of a pulsed signal 81 generated by the duty cycle control circuit 74. When a pulse is present, the voltage is high, and the transistor M1 is turned ON. When a pulse is not present, the voltage is low, and the transistor M1 is turned OFF.

Figure 5:
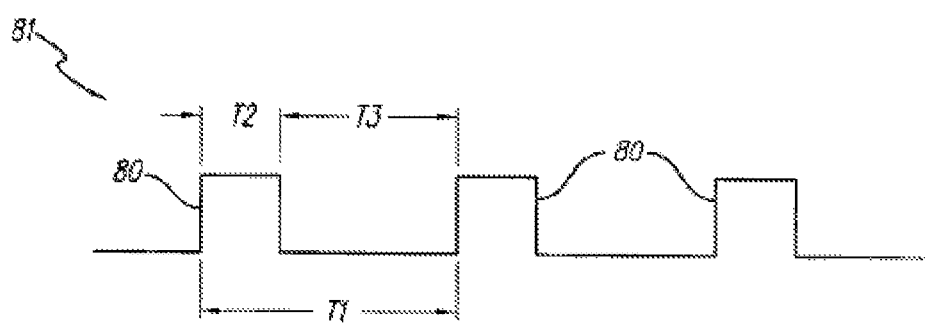
FIG. 5 is a waveform diagram that defines what is meant by Aduty cycle@ for purposes of the present application.

The ratio of time when the pulse is high to the total cycle time is known as the "duty cycle". The duty cycle is defined as shown in FIG. 5. As seen in FIG. 5, a pulsed signal 81 comprises a train of pulses 80. Each pulse 80 comprises a high voltage for a period of time T2 and a low voltage for a period of time T3. The total cycle time T1 is equal to T2 plus T3. Duty cycle is typically defined as a percentage and is computed as the ratio of T2/T1 or T2/(T2+T3). The duty cycle may thus vary from 0% when T1=0, to 100% when T1=T2.

The operation of the fly back circuit of FIG. 4 is known in the art. Basically, when transistor M1 is turned ON, during time period T2, circuit node 72 is connected to ground, which connects one side of the coil L1 to ground. This connection of one side of the coil L1 to ground causes an electrical current to start to flow from the power source 70 through the inductor coil L1. As soon as T2 ends, however, and for the remaining time T3 of the total cycle time T1, the node 72 floats (is not connected to ground), which causes the voltage at node 72 to step up to a high value (higher than the voltage of the power source VS, as electrical current continues to flow through coil L1, through diode D1, to charge capacitor C1. Thus, during time T2, current starts to flow through the coil L1, which causes electromagnetic energy to be stored in the coil. During time T3, this energy is transferred to capacitor C1, thus charging C1. Eventually, typically over several cycles, C1 is charged up to a voltage that is higher than the power source voltage VS. Capacitor C1 is blocked from discharging to ground through transistor M1 by diode D1 when M1 is turned ON during time T2. The stored charge held on capacitor C1 thus provides an output voltage VOUT (greater than VS) that causes an output current IO to flow through the load resistor RL.

The magnitude of the output voltage VOUT and output current IO may advantageously be controlled by adjusting the duty cycle of the signal 81. A higher duty cycle causes both VOUT and IO to increase, whereas a lower duty cycle causes VOUT and IO to decrease. Because the duty cycle is adjusted by controlling the pulse width (T2) of the pulses 80, the duty cycle control circuit 74 may also be referred to as a pulse width modulator circuit.

Still with reference to FIG. 4, it should also be noted that feedback may optionally be employed to better control and regulate the output voltage VOUT. That is, a sensing circuit 76A may be used to monitor the output voltage VOUT, and to compare the sensed output voltage to either a reference voltage VREF and/or a programmed reference signal PROG (which typically is presented to the sensing circuit 76A as a digital signal). The sensing circuit 76A generates a difference signal, on signal line 76C, representing the difference between the sensed output voltage VOUT and the reference voltage VREF and/or PROG. This difference signal controls a gate control circuit 76B, which modulates the gate of transistor M1 so as to drive the difference signal to zero.

Turning next to FIGS. 6A-6E, additional simplified schematic diagrams of circuits are illustrated that may be used in accordance with the present invention to achieve desired functions. More particularly, a voltage step up function may be achieved using the circuit shown in FIG. 6A; a voltage step down function may be achieved using the circuit of FIG. 6B; an energy reception function may be achieved using the circuit of FIG. 6C; a data reception function may be achieved using the circuit of FIG. 6D; and a data transmission function may be achieved using the circuit of FIG. 6E. Advantageously, many of the components used in the circuits of FIGS. 6A-6E may be the same. Common reference numerals are used to denote the components that may be the same. A brief explanation of each of these functions will next be described.

Figure 6A:
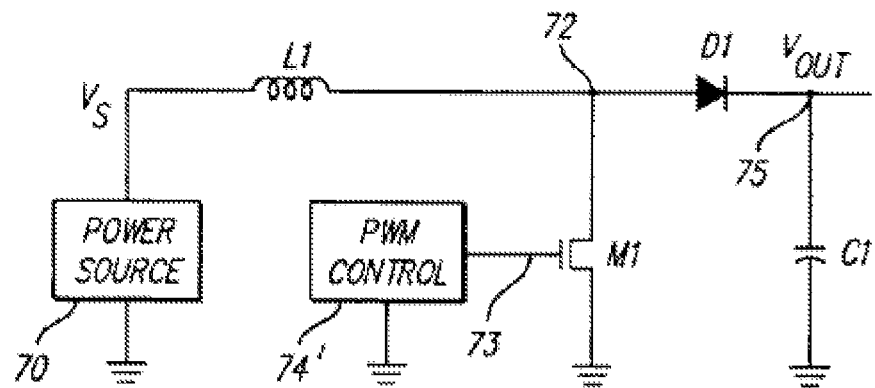
FIGS. 6A-6E illustrate simplified schematic diagrams of circuits that may be used in accordance with the present invention to respectively achieve the following implantable-device functions: voltage step up (FIG. 6A); voltage step down (FIG. 6B); energy reception (FIG. 6C); data reception (FIG. 6D); and data transmission (FIG. 6E)

FIG. 6A depicts a circuit that performs a voltage step up function. This circuit is substantially the same as the circuit previously described in connection with FIG. 4, except that the load resistance RL is not shown. However, it is to be understood that a load resistance may be present. It should also be understood that whereas FIG. 4 shows a duty cycle control circuit 74 controlling switch M1, FIG. 6A shows a PWM (pulse width modulation) control circuit 74' controlling switch M1. These circuits perform the same function (turning switch M1 ON or OFF) and, for purposes of the present invention, are substantially the same.

Figure 6B:
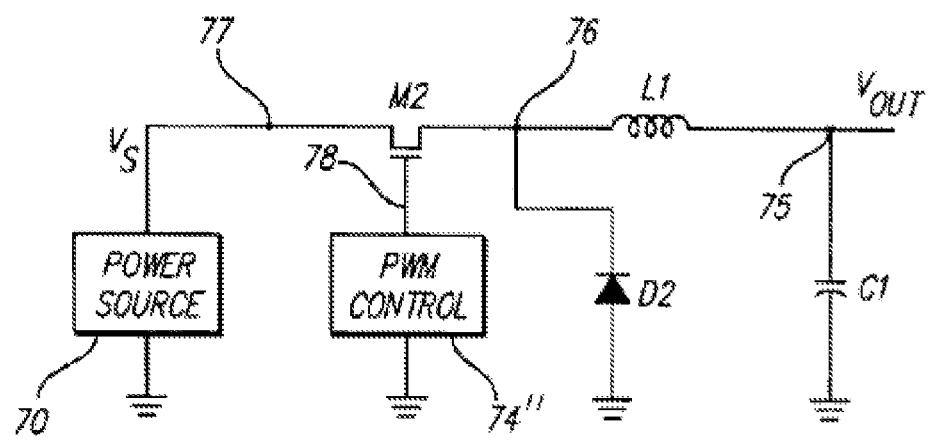

FIG. 6B depicts a circuit that performs a voltage step down function. As seen in FIG. 6B, a coil L1 is connected between circuit nodes 75 and 76. Node 75 represents the output node of the circuit whereon the output voltage VOUT is present. Capacitor C1 is connected between node 75 and ground. The anode side of a diode D2 is connected to node 76, while the cathode side of diode D2 is connected to ground. One leg of a transistor switch M2 is connected to node 76, while the other leg of transistor switch M2 is connected to the power source 70 at node 77. A gate terminal 78 of transistor M2 is connected to pulse-width modulation (PWM) control circuit 74".

Figure 6C:
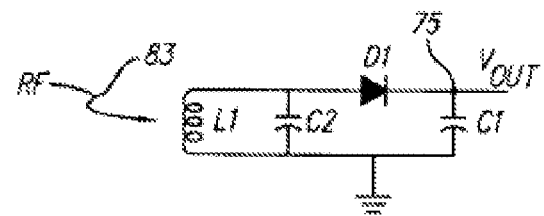

FIG. 6C shows a circuit that receives energy from an external source. The energy receive circuit shown in FIG. 6C includes a coil L1 having a capacitor C2 connected in parallel with the coil L1, with one side of the parallel connection being grounded. The coil L1 and capacitor C2 comprise an "LC" circuit that is tuned to the frequency of an incoming RF signal 83 (represented in FIG. 6C by a wavy arrow). Diode D1 is connected between output node 75 and the other side of the L1-C2 parallel connection, with the cathode of D1 being connected to node 75. Capacitor C1 is connected between output node 75 and ground.

In operation, the circuit shown in FIG. 6C receives the incoming RF signal 83 through coil L1, tuned to the frequency of the signal 83 by capacitor C2. Diode D1 rectifies the signal, storing the positive half cycles of the received signal 83 on capacitor C1. The voltage thus developed on capacitor C1 functions as an output voltage VOUT for use within the implant device.

Figure 6D:
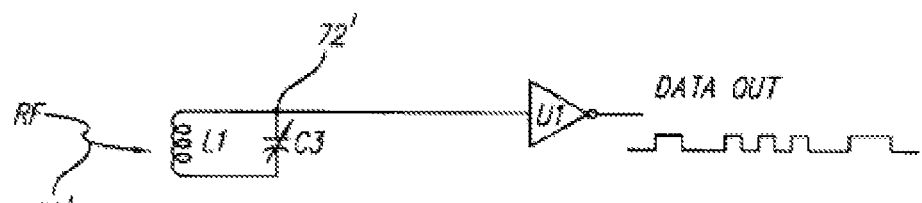

Next, in FIG. 6D, a data receiver circuit is illustrated. Such data receiver circuit includes coil L1 connected in parallel with variable capacitor C3. A modulated RF signal 88' is received through the coil L1. The value of C3 is adjusted, as required, so that the L1-C3 circuit is tuned to the frequency of modulation applied to the incoming RF signal 88'. Node 72', which represents an output node of the L1-C3 circuit, is connected to the input of an amplifier U1. The output signal provided by the amplifier U1 comprises a Data Out signal that reflects the modulation applied to the incoming modulated RF signal 88'.

Figure 6E:
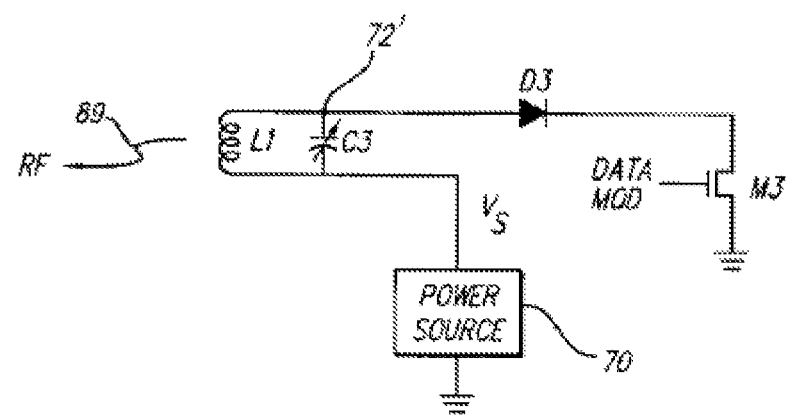

Turning to FIG. 6E, a simple data transmitter circuit is depicted. The data transmitter circuit includes a coil L1 connected in parallel with an adjustable variable capacitor C3. One side of the L1-C3 parallel connection is connected to a power source 70. The other side of the L1-C3 parallel connection, identified as node 72' in FIG. 6E, is connected to the anode of diode D3. The cathode of diode D3 is connected through a switch transistor M3 to ground. The gate terminal of switch M3 is driven by a "Data Mod" (data modulation) signal. Thus, in operation, when switch M3 is closed, a current is drawn through the L1-C3 parallel circuit. When switch M3 is open, no current is drawn through the L1-C3 parallel connection. The on-off current flow through the L1-C3 parallel connection causes a varying current to flow through coil L1 as controlled by the on-off pattern of the Data Mod signal. This current flow, as is known in the art, induces a varying magnetic field, which in turn causes an RF signal 89 to be radiated, or transmitted, from coil L1.

Thus it is seen that the circuits illustrated in FIGS. 6A-6E provide the functions of voltage step up (FIG. 6A), voltage step down (FIG. 6B), energy reception (FIG. 6C), data reception (FIG. 6D), and data transmission (FIG. 6E). All of these functions are typically required within an implantable stimulator device (FIG. 3).

Figure 7:
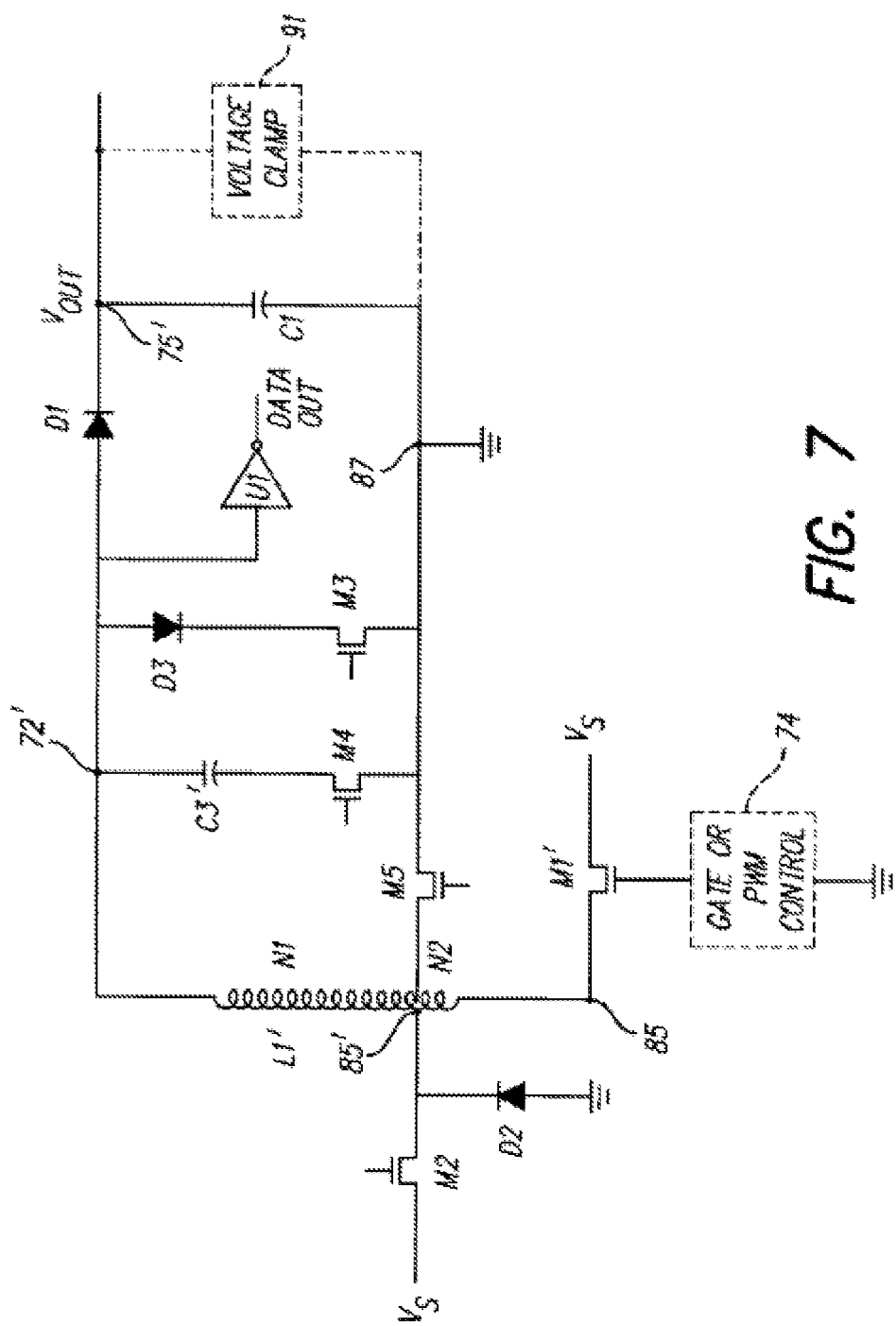
FIG. 7 is a simplified schematic diagram that illustrates a voltage converter circuit made in accordance with the present invention that selectively performs the five implantable-device functions illustrated in FIGS. 6A-6E.

In order to perform the functions provided by the circuits shown in FIGS. 6A-6E, while at the same time reducing the number of components needed for each function, and thereby reduce the overall size (and hence volume, weight and power) of the circuitry that carries out such functions, the present invention advantageously combines all the functions performed by the individual circuits shown in FIGS. 6A-6E into one circuit as shown in FIG. 7. Such combined circuit may be referred to as a "voltage converter using an RF-powering coil", and is particularly suited for use within an implantable medical device, such as an implantable neural stimulator.

Advantageously, the combined circuit provided by the present invention, and shown in FIG. 7, uses an RF-powering coil in combination with other circuit elements to perform the function of receiving RF power from an external source. The received RF power may be modulated in order to transmit control data into the circuit. Further, such RF-powering coil may be used to help transmit data out of the circuit. Significantly, the RF-coil used to receive power, data, and to transmit data, may also be used to selectively convert the received power (i.e., voltage) up or down in order to make operation of the circuit more efficient.

The circuit of FIG. 7 (i.e., the voltage converter circuit using an RF-powering coil provided by the present invention) includes a receiving/transmitting coil L1'. The coil L1' includes ends attached to circuit nodes 72' and 85, respectively. Node 85, in turn, is connected through transistor switch M1' to source voltage VS. The coil L1' further includes a tap point 85', where there are N2 turns of the coil between tap point 85' and node 85, and N1 turns between tap point 85' and node 72'. The coil L1' thus has a total of N turns, where N=N1+N2. Representative values of N1 are 10 to 100 turns, and for N2 are also 10 to 100 turns, and wherein the inductance of coil L1' is between about 10 to 100 microhenries (μH). However, in some embodiments, N1 and N2 may vary from 1 to 1000 turns, and L1' may vary between 1 to 1000 μH.

Still with reference to FIG. 7, a series combination of a capacitor C3' and transistor switch M4 is connected between circuit node 72' and tap point 85'. Another transistor switch M5 connects the tap point 85' of coil L1' to ground (node 87). Yet another transistor switch M2 connects the tap point 85' to the source voltage VS.

The cathode end of a diode D2 is also connected to the tap point 85' of the coil L1'; while the anode end of diode D2 is connected to ground.

The cathode end of another diode D3 is connected to node 72'. The anode end of diode D3 is connected through transistor switch M3 to ground (node 87). The anode end of diode D3 is also connected to the input of signal amplifier U1.

The cathode end of yet another diode D1 is also connected to node 72'. The anode end of diode D1 is connected to circuit node 75'. A capacitor C1 is connected between node 75' and ground (node 87). Circuit node 75' is the location where the output voltage VOUT is made available when the circuit operates in a voltage step up or step down mode. If needed, a suitable voltage clamp circuit 91 may be connected between node 75' and ground in order to prevent the voltage at the output node 75' from exceeding some predetermined value.

It is thus seen that the circuit of FIG. 7 includes five transistor switches, M1', M2, M3, M4 and M5. The state of these five switches, whether ON, OFF, or modulated with PWM data or signal data, determines which circuit function is performed as defined in the table presented in FIG. 8. That is, as seen in FIG. 8, in order for the circuit of FIG. 7 to operate in a voltage step up mode, switch M1' is turned ON, M2 is turned OFF, M3 is modulated with a PWM signal from a suitable duty cycle control circuit (see FIGS. 4 and 5), and both M4 and M5 are turned OFF. Under these conditions, the circuit of FIG. 7 effectively reduces to the circuit shown in FIG. 6A, with the only difference being diode D3 being added in series with switch M3 (which addition does not significantly alter the operation of the circuit). In such configuration and mode, the level of the output voltage VOUT is determined in large part by the duty cycle of the signal applied to the gate of transistor switch M3, as explained previously.

Similarly, as defined in FIG. 8, for the circuit of FIG. 7 to operate in a voltage step down mode, switch M1' is turned OFF, switch M2 is modulated with a PWM signal from a suitable duty cycle control circuit 74" (FIG. 6B), and switches M3, M4 and M5 are all turned OFF. Under these conditions, the circuit of FIG. 7 effectively reduces to the circuit shown in FIG. 6B, with the only difference being diode D1 connected between nodes 72' and 75' (which diode does not significantly alter the circuit's operation), and only a portion of coil L1' being used (i.e., only the turns N1 are used). In such configuration and mode, the circuit performs a voltage step down function, as described previously in connection with FIG. 6B.

As defined in FIG. 8, the circuit of FIG. 7 may also selectively operate in an energy receive mode and a data receive mode by turning switches M1', M2 and M3 OFF, and by turning switches M4 and M5 ON. With the switches in these positions, the circuit of FIG. 7 effectively reduces to the circuit shown in FIG. 6C, and to the circuit shown in FIG. 6D, with the only difference being that just a portion (N1 turns) of the coil L1' is used as part of the circuit. In this configuration and mode, the circuit of FIG. 7 thus performs both an energy receive function as described previously in connection with FIG. 6C, and a data receive function as described previously in connection with FIG. 6D.

As further defined in FIG. 8, the circuit of FIG. 7 may also selectively operate in a data transmit mode by turning switch M2 OFF, by modulating switch M3 with a data signal, and by turning switch M1' ON. Switch M4 may be either OFF or ON depending upon whether capacitor C3' is deemed necessary to better tune coil L1' for efficient data transmission. For many data transmissions, capacitor C3' should not be needed. Under these conditions, the circuit of FIG. 7 effectively reduces to the circuit shown in FIG. 6E. Hence, in such configuration and mode, the circuit performs a data transmit function, as described previously in connection with FIG. 6E.

Thus, it is seen that by selectively controlling the state of the switches M1', M2, M3, M4 and M5, the circuit of FIG. 7 may operate in any one of five different modes. Some of these modes, e.g., the energy receive mode and the data receive mode, may operate simultaneously. Others of the modes may be invoked in a time-multiplexed manner, e.g., with a first mode being followed by a second mode, and with the second mode being followed by a third mode, as required, depending upon the particular application at hand. Thus, for example, an energy and data receive mode may operate as a first mode to allow the device to receive operating power (e.g, to recharge a battery) and/or to receive initial programming control signals. This first mode may then be followed by a second mode, e.g., a voltage step up mode, initiated by changing the state of switches M1', M2, M3, M4 and M5 as defined in FIG. 8, during which the voltage of the primary power source is stepped up to a voltage needed by the device in order for it to perform its intended function. Subsequently, as required, a third mode, e.g., a data transmit mode, may be invoked in order to allow the implant device to transmit data to an external receiver.

The component values of the components, i.e., the transistor switches and capacitors and coil, used in the circuit of FIG. 7 may be readily ascertained by those of skill in the art for a particular application and desired RF frequency.

Figure 9:
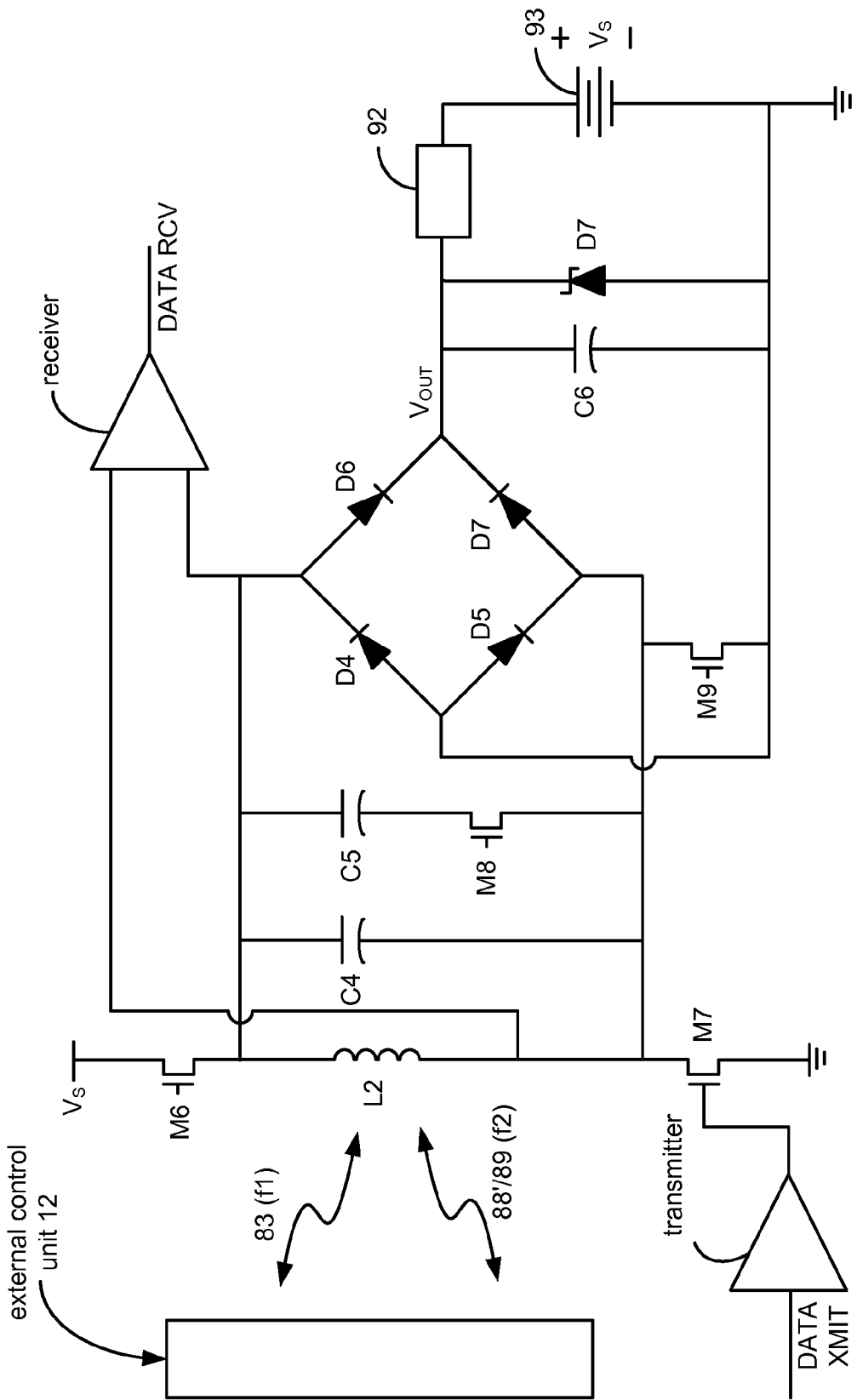
FIG. 9 is a simplified schematic diagram that illustrates a microstimulator with a single coil in accordance with one aspect of the present invention that can selectively charge or telemeter information to and from an external source, wherein the charging and telemetry may occur at different frequencies.

Another example of circuitry for an implantable medical device is shown in FIG. 9. Like the circuitry discussed earlier, the single-coil circuitry of FIG. 9 can receive and transmit data, and can receive power for charging the implantable medical device. Also similar is the tunable nature of the circuitry, which like earlier circuitry can be tuned to one frequency for data transmission and reception, and to another for power reception. The circuitry of FIG. 9 can also use the single coil to perform the step up and step down features previously discussed, although those aspects of the circuitry are not shown.

The circuit of FIG. 9 includes coil L2. The coil L2 is connected at one end through transistor switch M6 to power source voltage VS and at the other end through transistor switch M7 to ground. C4 is connected in parallel with coil L2. A series combination of a capacitor C5 and transistor switch M8 are also connected in parallel to coil L2. Also connected in parallel with coil L2 is the full bridge rectifier represented by diodes D4, D5, D6, and D7 for producing DC voltage VOUT. Overall transfer efficiency is expected to be about 15% higher for a full bridge rectifier compared to a single diode, or half-wave, rectifier. However, such other alternatives could also be used to produce VOUT. A transistor switch M9 is also connected between the rectifier circuitry and ground.

DC voltage VOUT is received at storage capacitor C6, which smoothes the voltage before being passed to charging circuitry 92. Charging circuitry 92 is used to charge battery source 93 in a controlled fashion. If needed, a Zener diode D7 or other suitable voltage clamp circuit may be connected across capacitor C6 to prevent VOUT from exceeding some predetermined value.

FIG. 10 shows the status of transistor switches, M6, M7, M8 and M9 for the energy receive, data receive, and data transmit modes. As seen in FIG. 10, for the circuit of FIG. 9 to operate in an energy receive mode, the circuit will turn switches M6, M7 and M9 OFF, and will turn switch M8 ON. Turning M8 ON includes capacitor C5 in parallel with capacitor C4, which, in conjunction with the inductance formed by the coil L2, forms a resonant circuit which is tuned to the frequency f1 of the RF signal 83 sent from external control unit 12. Such frequency f1 can be approximately 80 kHz for example.

The circuit of FIG. 9 may also operate in a data transmit mode during charging by employing back telemetry known as Load Shift Keying (LSK). As is described in greater detail in U.S. application Ser. No. 12/354,406, filed Jan. 15, 2009, during LSK, the impedance of the resonant circuit shown in FIG. 9 is modulated via control of transistor switch M9, with the transistor's on-resistance providing the necessary modulation. This change in impedance is reflected back to the coil in the external control unit 12 which produces the RF signal 83, which reflection is demodulated at the external control unit 12 to recover the transmitted data. This means of transmitting data is useful to communicate data relevant during charging of the battery 93 in the microstimulator, such as the capacity of the battery, whether charging is complete and the external charger can cease, and other pertinent charging variables.

For the circuit of FIG. 9 to operate in a data receive mode, the circuit will turn switches M6, M8 and M9 OFF, and will turn switch M7 ON. Turning M8 off excludes capacitor C5 from the resonant circuit, whose tuning is thus governed by coil L2 and capacitor C4. With capacitor C5 excluded, the resonant circuit is tuned to a higher frequency f2 matching the modulated RF signal 88' received from the external control unit 12. (The external control unit 12 that sends the RF data signal 88' can be the same device as, or separate from, the external control unit that sends the RF power signal 83 to the microstimulator. Even though the external control unit 12 can comprise more than one device, the external control unit 12 is however shown as a singular device in FIG. 9 for convenience). For example, f2 can comprise approximately 125 kHz, which can comprise a center frequency of the modulated data in the RF signal 88'. For example, if the RF signal 88' is modulated in accordance with a Frequency Shift Keying (FSK) protocol, a logic '0' might comprise a frequency slightly lower than the center frequency (e.g., 121 kHz), while a logic '1' might comprise a frequency slightly higher than the center frequency (e.g., 129 kHz); despite the slight difference, this range or band of frequencies for the data can be discussed as a single frequency. Turning M7 ON grounds the resonant circuit, which provides an input to the receiver, which demodulates the received data. The receiver can either comprise a differential input as illustrated in FIG. 9, or can comprise a single-ended non-differential input.

As further shown in FIG. 10, the circuit of FIG. 9 may also operate in a data transmit mode by turning switches M8 and M9 OFF, by modulating switch M7 with a data signal, and by turning switch M6 ON. Under these conditions, the resonant circuit is once again, by virtue of transistor M8 being off, tuned to the higher frequency f2, and will broadcast an RF signal 89 to the external control unit 12 accordingly, with the energy for the radiation being supplied from the power source voltage Vs via transistor M6. The data appearing at transistor M7 will be modulated by a transmitter in accordance with the tuning of the resonant circuit, and so will center around 125 kHz. For example, when transmitting a logic '0', the data signal presented to transistor M7 might comprise a 121 kHz signal, or might comprise a 129 kHz signal when transmitting a logic '1.' The transmitter could also couple to transistor M6.

Thus, it is seen that by selectively controlling the state of the switches M6, M7, M8 and M9, the circuit of FIG. 9 may operate in different modes. Such modes may be invoked in a time-multiplexed manner, e.g., with a first mode being followed by a second mode, depending upon the particular application at hand. Advantageously, tuning allows charging at a first frequency f1 and data telemetry at a second frequency f2. Because lower frequencies, e.g., 80 kHz, have been found to be more optimal for charging than are higher frequencies due to heating concerns, and because higher frequencies, e.g., 125 kHz, have been found to allow for increased bandwidth and higher data rates, the circuitry of FIG. 9, like other tunable circuits disclosed herein, provides a design that is optimized for both charging and telemetry while still using only a single coil for both. A variable capacitor could be used in place of capacitors C4 and C5 to achieve similar tuning.

It is thus seen that the invention described herein provides a voltage converter circuit for use within an implantable device, e.g., such as an implantable microstimulator or similar type of neural stimulator, that is compact, efficient, and provides a wide range of output voltages and currents.

It is further seen that the invention provides a voltage converter circuit that avoids the use of a network of capacitors switched between parallel and series, or other, configurations in order to provide the step up and step down voltage conversion function.

It is further seen that the invention provides an implantable device containing a single coil that is tunable to different frequencies for charging and telemetry.

While the invention herein disclosed has been described by means of specific embodiments and applications thereof, numerous modifications and variations could be made thereto by those skilled in the art without departing from the scope of the invention set forth in the claims.

What is claimed is:

1. An implantable medical device, comprising:
   an implantable housing;
   a battery within the housing having a battery voltage;
   electrical circuitry within the housing; and
   a coil,
   wherein the electrical circuitry is configurable to form a first circuit including the coil to receive power from an external source to charge the battery, and
   wherein the electrical circuitry is configurable to form at least one second circuit including the coil to convert the battery voltage to a different voltage level.

2. The implantable medical device of claim 1, wherein the electrical circuitry is configurable to form a third circuit including the coil to receive command information or data information from an external source.

3. The implantable medical device of claim 2, wherein the electrical circuitry is configurable to form a fourth circuit including the coil to transmit data to an external source.

4. The implantable medical device of claim 1, wherein the at least one second circuit including the coil converts the battery voltage to a different voltage level that is lower than the battery voltage.

5. The implantable medical device of claim 1, wherein the at least one second circuit including the coil converts the battery voltage to a different voltage level that is higher than the battery voltage.

6. The implantable medical device of claim 1, wherein the electrical circuitry is configurable to form two second circuits including the coil, wherein a first of the second circuits converts the battery voltage to a different voltage level that is lower than the battery voltage, and wherein a second of the second circuits converts the battery voltage to a different voltage level that is higher than the battery voltage.

7. The implantable medical device of claim 1, wherein the electrical circuitry is configurable to form the first circuit and the at least one second circuit at different times.

8. An implantable medical device, comprising:
   an implantable housing;
   a battery within the housing having a battery voltage;
   electrical circuitry within the housing; and
   a coil,
   wherein the electrical circuitry is configurable to form a first circuit including the coil to receive command information or data information from an external source, and
   wherein the electrical circuitry is configurable to form at least one second circuit including the coil to convert the battery voltage to a different voltage level.

9. The implantable medical device of claim 8, wherein the electrical circuitry is configurable to form a third circuit including the coil to transmit data to an external source.

10. The implantable medical device of claim 8, wherein the at least one second circuit including the coil converts the battery voltage to a different voltage level that is lower than the battery voltage.

11. The implantable medical device of claim 8, wherein the at least one second circuit including the coil converts the battery voltage to a different voltage level that is higher than the battery voltage.

12. The implantable medical device of claim 8, wherein the electrical circuitry is configurable to form two second circuits including the coil, wherein a first of the second circuits converts the battery voltage to a different voltage level that is lower than the battery voltage, and wherein a second of the second circuits converts the battery voltage to a different voltage level that is higher than the battery voltage.

13. The implantable medical device of claim 8, wherein the electrical circuitry is configurable to form the first circuit and the at least one second circuit at different times.

14. A method for operating an implantable medical device having electrical circuitry including a coil and a battery having a battery voltage, the method comprising:
operating the implantable medical device in at least two of the following modes:
(i) a first mode in which the electrical circuitry is configured to use the coil to receive power from an external power source to charge the battery;
(ii) a second mode in which the electrical circuitry is configured to use the coil to communicate with an external source; and
(iii) a third mode in which the electrical circuitry is configured to use the coil to convert the battery voltage to a different voltage level,
wherein operation in each mode is time multiplexed such that the coil is used with only one mode at a time.

15. The method of claim 14, wherein the implantable medical device operates in the first, second, and third modes.

16. The method of claim 14, wherein during the second mode the electrical circuitry is configured to use the coil to receive command information or data information from an external source, or to transmit data to an external source.

17. The method of claim 14, wherein during the second mode the electrical circuitry is configured to use the coil to receive command information or data information from an external source, and to transmit data to an external source.

18. The method of claim 17, wherein receiving the command information or data information and transmitting the data is time multiplexed such that the coil is used with only one of the receiving or transmitting at a time.

19. The method of claim 14, wherein the battery voltage is converted to a different voltage level that is higher than the battery voltage.

20. The method of claim 14, wherein the battery voltage is converted to a different voltage that can be higher or lower than the battery voltage, wherein the conversion is time multiplexed such that the coil is used to convert to either the higher or the lower different voltage at a time.

* * * * *